United States Patent [19]
>
> Goodale et al.

[11] 4,296,634

[45] Oct. 27, 1981

[54] SEPTUM FOR USE IN GAS CHROMATOGRAPHY AND METHOD OF OPERATION

[76] Inventors: Robert H. Goodale, 7355 Yucca Ct., Boulder, Colo. 80301; George M. DuJack, Jr., 391 Fourth St., Troy, N.Y. 12180

[21] Appl. No.: 122,916

[22] Filed: Feb. 20, 1980

[51] Int. Cl.³ .......................................... G01N 37/00
[52] U.S. Cl. .................................................. 73/864.86
[58] Field of Search ................................... 73/422 GC

[56] References Cited

U.S. PATENT DOCUMENTS 3,482,450  12/1969  Harris, Sr. et al. ............ 73/422 GC

FOREIGN PATENT DOCUMENTS 108750  6/1964  Norway ......................... 73/422 GC Primary Examiner—S. Clement Swisher
Attorney, Agent, or Firm—O'Rourke & Harris

[57] ABSTRACT

Septum for use in relatively high temperature gas chromatography including within the septum a cooling element, preferably a fluid carrying loop through which heat transfer medium may be circulated, to lower the temperature of the septum thus avoiding excessive bleed of volatile compounds into the carrier gas stream and protecting the septum from rapid thermal degradation.

16 Claims, 7 Drawing Figures

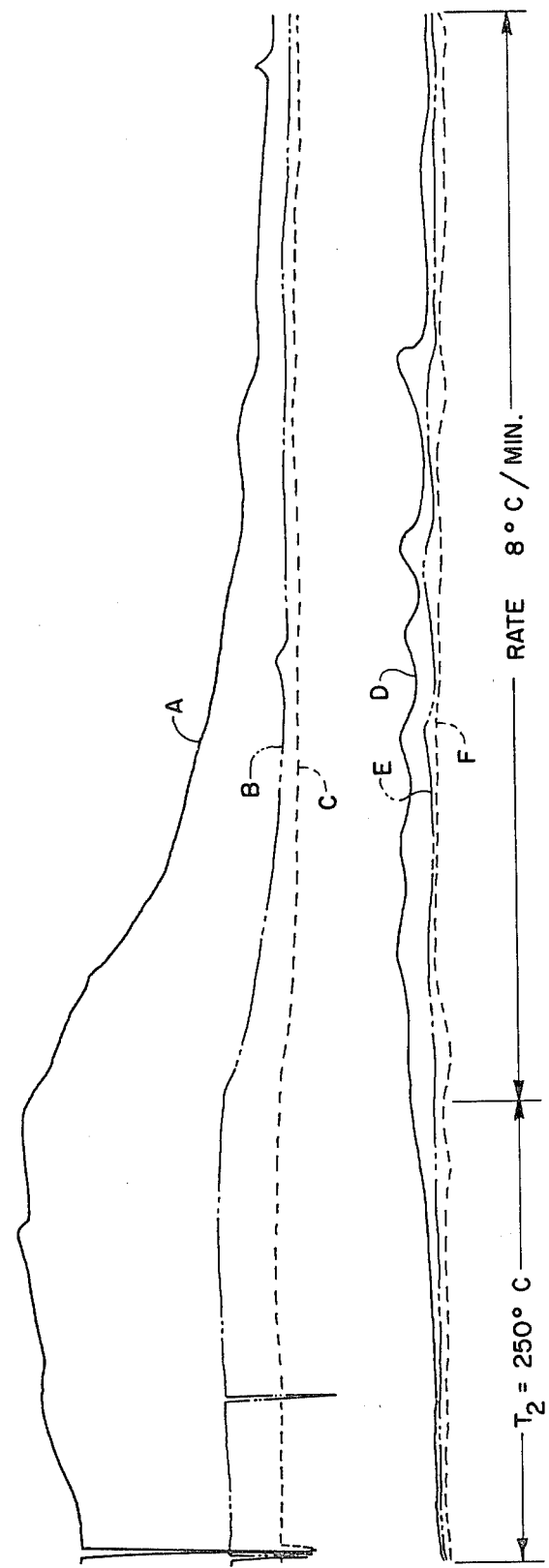

SEPTUM FOR USE IN GAS CHROMATOGRAPHY AND METHOD OF OPERATION

BACKGROUND OF THE INVENTION

The present invention relates generally to septums adapted to isolate the carrier gas of gas chromatography apparatus from the atmosphere and through which samples may be injected by, for instance, puncturing the septum with a syringe needle. More particularly, the invention relates to a septum including internal cooling means to minimize the temperature of the septum when exposed to relatively high column temperatures.

DESCRIPTION OF THE RELATED ART

Gas chromatography is a well known and highly developed art. In many instances, chromatographic columns operate at temperatures on the order of 200° C. or higher to avoid undesirable condensation of the samples. It has been recognized that at such temperatures volatile compounds bleed from elastomeric septa employed to seal a column from the atmosphere while providing access by a puncturing needle to inject samples. Concurrently, elevated temperatures induce degradation of the septum. Various approaches have been taken to minimizing these problems. Often, a fresh septum is solvent washed and baked to drive off volatile compounds. However, when the septum is punctured by a needle, fresh areas are exposed. Also, bits of temperature weakened septum material may be carried with the needle. Thus, after a limited number of injections, bleed often increases even in the event of a thoroughly baked septum.

At the temperature of concern, the septum both off-gases uncrosslinked polymer or residual monomer and undergoes basic degradation of the polymeric chain forming the elastomer. Thus baking is but a short term aid which minimizes bleed but may acelerate thermal degradation.

Other devices, including fluoropolymeric surfaces on a silicon rubber septum, guides to limit the injection needle to the same puncture opening, and inert coverings, such as a metal foil, have served to limit bleed while not eliminating the phenomenon.

Attempts have been made to fit a septum cooler to the injection port of a column. Such septum coolers have been secured around the metal fitting in which the septum is held and accordingly conducted heat from such fitting. While some decreases in bleed have been reported, the heat carried from the metal portion of the injection port also caused a low temperature condition at the junction of the injection port with the carrier gas. Since the purpose of high temperature chromatography is to maintain high boiling samples in a gaseous state, such cooling tended to induce condensation of the sample at the injection port. Since the metal surrounding the septum has a much greater heat conductivity than the rubber septum, the injection port cooler tended to cool the metal fitting rather than the septum.

SUMMARY OF THE INVENTION

The present invention, which provides a heretofore unavailable improvement over previous septa for use in high temperature gas chromatography, includes within the septum proper a cooling element which serves to lower the temperature of the septum while not appreciably lowering the temperature of the injection port. The method and structure involves the septum structure per se, and thus differs substantially from previous injection port cooling concepts.

Accordingly, an object of the present invention is to provide a new and improved method and septum structure for high temperature gas chromatographic columns which provide for lower temperature operation of the septum while not appreciably lowering the temperature of the injection port at the point of exposure to the heated carrier gas.

Another object of the present invention is to provide a new and improved septum and method of cooling which substantially eliminates bleed under high temperature chromatographic conditions.

Yet another object of the present invention is to provide a new and improved method and structure for chromatographic septa which enhances the life of the septa under high temperature operating conditions.

These and other objects and features of the present invention will become apparent from the following description.

BRIEF DESCRIPTION OF THE DRAWINGS

In the drawings:

FIG. 7 is a representation of six traces of the peaks recorded in a chromatographic column utilizing a septum cooled in accord with the instant invention, and a septum without benefit of cooling.

DETAILED DESCRIPTION OF THE DRAWINGS

Figure 1:
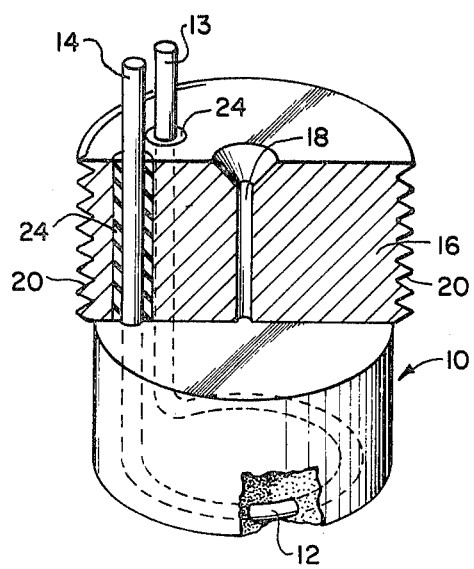
FIG. 1 is a partially cutaway perspective view of a septum and fitting in accord with the instant invention.
Figure 2:
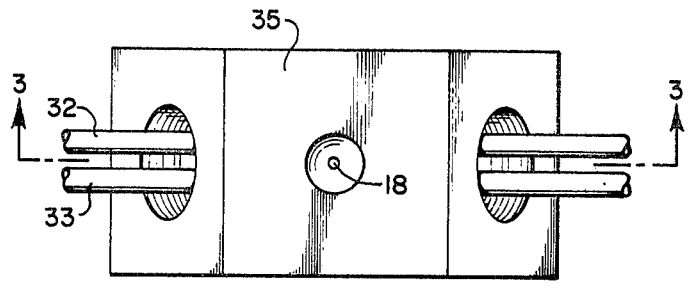
FIG. 2 is a top view of an injection port adapted to secure the septum illustrated in FIGS. 3 through 5.
Figure 3:
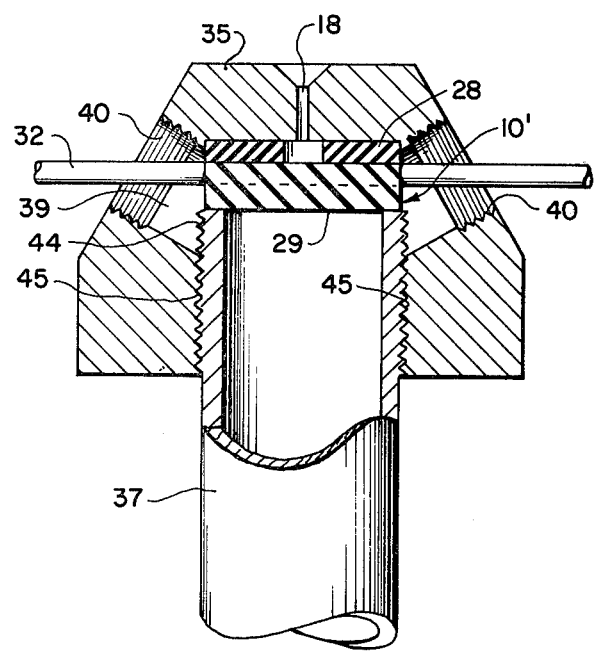
FIG. 3 is a section view along section line III—III of an injection port including a septum and cooling means in accord with the instant invention.

Turning now to the drawings, wherein like components are designated by like reference numerals through the various figures, a septum in accord with the instant invention is illustrated in FIG. 1 and generally designated by reference numeral 10. As shown in FIG. 1, septum 10 is a disk shaped member of resilient material, and preferably of silicone rubber. Septum 10, as is well known, is adapted to fit in the injection port of a chromatographic device (not shown) such that samples may be injected by inserting a syringe needle through septum 10. Cooling means, such as cooling loop 12, is positioned within septum 10 and includes inlet conduit 13 and outlet conduit 14. Thus, septum 10 may be protected from extreme temperatures by flowing a cooling fluid, such as a chilled water mixture, through inlet conduit 13 around cooling loop 12 and out conduit 14. In this manner heat is carried away from septum 10, and particularly from the portion thereof within cooling loop 12. Packing member 16, having guide channel 18 defined therethrough, is adapted to bear against septum 10 by means of a forces generated by threaded portion 20 which engages complementary threads on the injection port (not shown). Opening 24 is defined in packing member 16 to accomodate inlet and outlet conduits 13 and 14, respectively. Thus, in operation, a syringe needle will be guided by channel 18 to a common puncture path through septum 10. Such septum puncture path is within cooling loop 12 and thus at the portion of septum 10 maintained at a lowered temperature by cooling loop 12. Since packing member 16 is of metal, and since it is not desirable to unduly cool the metal portion of the injection port, inlet conduit 13 and outlet conduit 14 may be insulated with a material of relatively low heat conductivity such as air, an elastomeric substance or a foam material at opening 24. Septum 10 of FIG. 1 is effective for its purposes, but of greater cost than conventional septa in that cooling loop 12 would be molded in disposable septum 10. As shown in FIGS. 2 and 3, septum 10 may be formed of two pieces. Septum 10, as illustrated, is formed of ring member 28 and replaceable septum member 29. Cooling tubes 32 and 33, as is apparent from FIGS. 2 and 3, are disposed between ring member 28 which is preferably of low heat conductivity, and replaceable septum member 29, but removable therefrom when injection block 35 is removed from injection port member 37. Since, septum member 29 is primarily exposed to the elevated temperatures of the carrier gas of the chromatographic device, and since septum member 29 also is positioned to be punctured by an injection needle passing through guide channel 18, it is clear that septum member 29 would incur degradation and be subject to wear much more rapidly than ring member 28. Thus, when required, septum member 29 can readily be replaced, cooling tubes 32 and 33 positioned to protect and cool septum member 29, and ring member 28 positioned to secure cooling tubes 32 and 33. Since cooling tubes 32 and 33 are not subject to wear, relatively cheaply manufactured septum member 29 constitutes the primary expendable portion of septum 10 as illustrated in FIGS. 2 through 5. Of course ring member 28 can be replaced with a solid member which would be punctured by an injection needle.

Other features of the embodiment illustrated in FIGS. 2 and 3 include openings 39 defined in opposite sides of injection block 35 to accommodate cooling tubes 32 and 33. Threaded portions 40 are included therein in event insulating members (not shown) are provided to locate cooling tubes 32 and 33 in openings 39 and injection block 35. Cooling tubes 32 and 33 are shown only with regard to the interface with septum 10', but it is to be understood that the tubes are connected to a source of cooling fluid, such as ice water, and that cooling tubes 32 and 33 may be a common loop or parallel legs of a common flow path. To replace septum member 29, injection port member 37 and injection block 35 are separated by disengaging threaded portions 44 and 45 of injection port member 37 and injection block 35, respectively. This frees septum member 29 for removal and replacement. Normally, ring member 28 would not be replaced as frequently as septum member 29, but replacement would obviously be readily accomplished.

Figure 4:
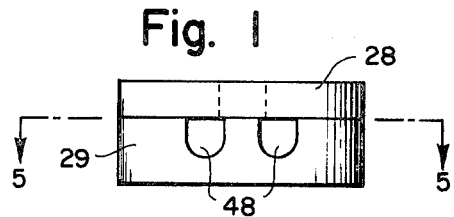
FIG. 4 is a side view of a septum adapted for use in the apparatus illustrated in FIGS. 2 and 3.
Figure 5:
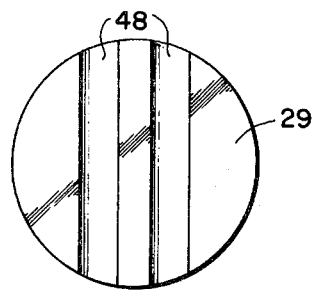
FIG. 5 is a top view of the septum of FIG. 4.

The details of septum member 29 are apparent from the illustration of FIGS. 4 and 5. As shown, grooves 48 are defined in septum member 28 to accomodate cooling tubes 32 and 33. Septum member 29 is positioned as shown in FIG. 3. Guide channel 18 would locate an injection needle to pierce septum member 29 between adjacent grooves 48, and accordingly at the cooled portion of septum member 29. It will be noted that openings 39 in injection block 35 are positioned to isolate cooling tubes 32 and 33 and the adjacent cooled portion of septum 10' as shown in FIG. 3, from metal components of the injection port.

Figure 6:
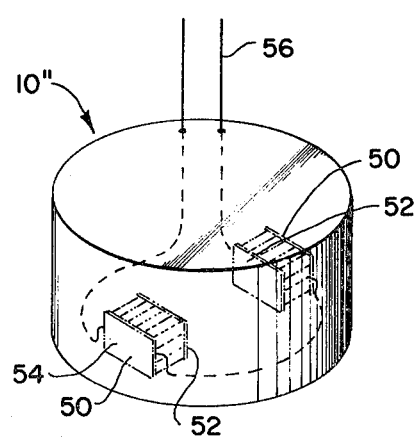
FIG. 6 is a perspective view illustrating yet another embodiment of a septum in accord with the instant invention.

Yet another embodiment of the instant invention is illustrated in FIG. 6 wherein septum 10" is somewhat similar to that of septum 10, illustrated in FIG. 1, with the exception that a pair of Peltier effect thermo coolers 50 are provided with the cold base 52 thereof adjacent the interior of septum 10" and the hot base 54 thereof adjacent the exterior of septum 10", whereby heat may be conducted from the interior to the exterior of septum 10" and transfered therefrom by cooling means (not shown) such as cooling fins, cooling coils, etc. Septum 10" could of course be mounted as shown in FIGS. 1 or 3 with the hot base 54 of thermo electric cooler 50 being isolated from surrounding injection port components. Wire 56 may be provided to power thermo electric coolers 50. While the preferred embodiment is other than that shown in FIG. 6, it is to be understood that cooling means of any nature are suitable for use with the instant invention. The significant aspect of the instant invention is the cooling of the septum per se, and particularly cooling at the internal portion whereat the needle pierces the septum. Further, cooling means must be substantially isolated from the injection port proper to avoid condensation of components in the gas stream.

From the above discussion it is apparent that septum 10 including a cooling means, either cooling loop 12, cooling tubes 32 and 33, coolers 50 or other functionally equivalent expedients, provides for conduction of heat from septum 10. Since the resilient materials from which septum 10 are conventionally manufactured display rather low heat conductivity, substantial amounts of heat will not be drawn from surrounding metal constituting the injection port, and the temperature at the injection port past which the carrier gas flows will not be appreciably lowered. Instead, only critical portions of septum 10 will be cooled to minimize degradation of septum 10 and off-gasing of volatile materials therefrom. In this manner, deleterious results from such off-gasing and/or leakage through septum 10 are substantially lessened.

As shown in FIG. 7, and discussed below, experimental results confirm the effectiveness of the septum in accord with the instant invention.

OPERATION OF THE INVENTION

A number of tests of septa were conducted using a Hewlett-Packard 5710A chromatographic apparatus with F.I.D. (detector).

Initially, comparative tests of actual injection port temperatures vis-a-vis injection port temperature settings were conducted to determine if a cooled septum would adversely affect injection port temperatures. For purposes of the tests, a septum having a thermocouple mounted adjacent thereto and a pair of 1/16 inch brass tubes positioned transversely therethrough as shown in FIGS. 3 and 4 was utilized. The thermocouple was positioned 2 inches below the septum, and a series of readings were taken as illustrated in the following table. Cooling fluid at a temperature of about 18° C. to 28° C. was circulated through the brass tubing during the test, and similar readings were taken with no coolant flow.

TABLE

| NO COOLER | |
|---|---|
| Injection Port Setting (°C.) | Thermocouple Reading (°C.) |
| 200 | 190 |

TABLE-continued

| | |
|---|---|
| 250 | 235 |
| 300 | 282 |
| 350 | 327 |
| 400 | 370 |

COOLER

| Injection Port Setting (°C.) | Thermocouple Reading (°C.) |
|---|---|
| 200 | 190 |
| 250 | 235 |
| 300 | 285 |
| 350 | 330 |
| 400 | 370 |

Thus, it was demonstrated that the septum cooler had little or no effect on the injection port temperature.

Two commercial silicone septa, i.e. Microsep* F-402 were identically prepared by washing in distilled water, filtered acetone and hexane. The septa were then baked for one hour at 200° F. Septa were mounted as described above with one in contact with a pair of 1/16 inch brass tubes carrying cooling fluid, and the other without benefit of cooling. Two sets of detector tracings were obtained utilizing four runs for each. In both instances, the column was initially operated at 80° C. for 8 minutes, and then the temperature advanced at the rate of 8° C. per minute until a temperature of 250° C. was reached, whereupon such temperature was maintained for 8 minutes. The injection port was set at 250° C. as was the detector. Sixty milliliters per minute of nitrogen gas was flowed without sample and a chart speed of 1 centimeter per minute was utilized.
*Registered Trademark Canton Bio-Medical Products, Inc.

As shown in FIG. 7, three tracings from each run were noted. In both instances, the first run was utilized to condition the septum and the column with data being recorded only during the last three runs.

With reference to FIG. 7, traces A, B and C were recorded with a setting of range 10, with trace A at an attenuation of 16, trace B at an attenuation of 32, a trace C at an attenuation of 64. Traces, which are read from right to left, should be flat since no sample was included in the carrier gas. However, a number of peaks and curve elevations were noted indicating off-gasing from the septum.

Traces E, D and F were developed utilizing identical conditions to those of traces A, B and C, except that the column was set at range 1, i.e. an order of magnatude more sensitive than range 10, and the brass tubes through the septum carried a cooling fluid from a bath at a temperature of −35° C. Trace D was run at an attenuation of 8, trace E was run at an attenuation of 16, and trace F was run at an attenuation of 32.

The latter set of traces, despite being at a sensitivity 10 times that of the former set, display a flatness and absence of spurious peaks. Traces C and F both display desirable base lines characteristics, but trace F, utilizing septum coolant, was obtained with the substantially higher sensitivity.

In summary, the instant invention provides a septum structure which affords substantially enhanced septum performance in the form of reduced off-gasing which provides for greater sensitivity, and prolonged septum life. This is accomplished without substantially altering the injection port temperature.

Although only several embodiments of the present invention have been illustrated and described, it is anticipated that various changes and modifications will be apparent to those skilled in the art, and that such changes may be made without departing from the scope of the invention as defined by the following claims.

What is claimed is:

1. A septum for use in gas chromatographic apparatus, the septum comprising,
   a septum member of an elastomeric material, and
   cooling means positioned internally of the septum member, whereby the temperature of the septum may be maintained at a lowered level when exposed to column gases at elevated temperatures while avoiding substantial cooling of such gases by the septum.

2. A septum as set forth in claim 1 in which the cooling means comprise a tubular cooling coil adapted to conduct a coolant, the cooling coil being positioned adjacent but spaced from the central portion of the septum member, whereby an injection needle may be inserted through the central portion of the septum member.

3. A septum as set forth in claim 1 in which the cooling means comprise thermo electric coolers.

4. A septum as set forth in claim 1 in which the septum member is comprised of first and second members with the cooling means being positioned within the septum member adjacent the parting surface line between the upper and lower members.

5. A septum as set forth in claim 4 in which grooves are defined in at least one of the first and second members comprising the septum member, the grooves being configured to receive and support the cooling means in heat transfer relationship with the septum member.

6. A septum as set forth in claim 4 in which at least one of the upper and lower members is a ring member whereby the ring member may be positioned to secure the cooling means while allowing an injection needle to puncture the other of the upper and lower members through the opening defined in the ring member.

7. A septum for use with gases at elevated temperatures in gas chromatographic apparatus, the septum comprising,
   a septum member of elastomeric material,
   an opening defined in the septum member and adapted to accomodate in heat transfer relationship cooling means, the opening defined in the septum member being positioned internally of the septum member adjacent the central portion thereof.

8. A septum as set forth in claim 7 in which the septum member is cylindrical in shape.

9. A septum as set forth in claim 8 in which the opening defined in the septum member comprise at least one groove defined therethrough.

10. A septum as set forth in claim 9 in which the septum member is formed of first and second members, with the parting faces thereof being substantially perpendicular to the axis of the cylindrical septum member and in which the grooves are defined adjacent to an opening to the interface between the first and second members.

11. A septum as set forth in claim 10 in which at least one of the first and second members comprise a ring member having a central annular opening.

12. In a gas chromatographic apparatus having a metal injection port with an elastomeric septum secured in the injection port and adapted to seal the interior of the apparatus from the atmosphere, the improvement comprising cooling means positioned internally within the septum member and substantially isolated from the metal members of the injection port, whereby the septum member may be maintained at a lowered internal temperature while maintaining the injection port at the desired elevated temperature.

13. The improvements set forth in claim 12 wherein the cooling means comprise at least one cooling tube positioned through the septum and isolated from the metal portion of the injection port.

14. A method for cooling a septum positioned in a metal injection port of a gas chromatographic apparatus adapted to operate at high temperature, the method comprising, conducting heated gases through the chromatographic apparatus and over one surface of the septum, withdrawing heat from the internal portion of the septum by cooling means isolated from the metal injection port, and maintaining the internal portion of the septum at a lowered temperature while maintaining the injection port at an elevated temperature corresponding substantially to that of the flowing gas.

15. A method as set forth in claim 14 in which the heat is conducted from the internal portion of the septum by flowing a coolant fluid through a tubular member positioned within the septum member.

16. A method as set forth in claim 14 in which the heat is conducted from the internal portion of the septum by thermo electric coolers positioned with the cool face thereof internally of the septum.

* * * * *